United States Patent [19]

Baba et al.

[11] Patent Number: 5,266,595

[45] Date of Patent: Nov. 30, 1993

[54] METHOD FOR TREATMENT OF CYSTINURIA

[75] Inventors: Hisashi Baba, Toyonaka; Hideo Takashina, Kobe, both of Japan

[73] Assignee: Santen Pharmaceutical Co., Ltd., Osaka, Japan

[21] Appl. No.: 997,605

[22] Filed: Dec. 28, 1992

[30] Foreign Application Priority Data

Jan. 10, 1992 [JP] Japan .................................. 4-40037

[51] Int. Cl.⁵ .......................................... A61K 31/195
[52] U.S. Cl. ..................................... 514/562; 514/891
[58] Field of Search .............................. 514/562, 891

[56] References Cited

PUBLICATIONS

Chemical Abstracts 115:248063e, 1991, Kojima et al.
Chemical Abstracts 114:220968j, 1991, Nakajima et al.

Primary Examiner—Jerome D. Goldberg
Assistant Examiner—Minna Moezie
Attorney, Agent, or Firm—Frishauf, Holtz, Goodman & Woodward

[57] ABSTRACT

A method for treatment of cystinuria which comprises administering to a patient in need thereof an effective amount of bucillamine or a pharmaceutically acceptable salt thereof.

10 Claims, No Drawings

METHOD FOR TREATMENT OF CYSTINURIA

FIELD OF THE INVENTION

This invention relates to a method for treatment of cystinuria by administration of bucillamine or pharmaceutically acceptable salts thereof.

BACKGROUND OF THE INVENTION

Cystinuria is a disease caused by congential metabolic disorders wherein the reabsorbing function of cystine, lysine, ornithine and arginine into renal tubules is hereditarily damaged and an excessive amount of amino acids are excreted into urine. Amino acids except cystine are soluble in urine and do not cause a problem. Cystine, however, is very slightly soluble in urine and crystallizes to form stones in the urinary tract. The main direct complaints of cystinuria patients are colic, hematuria, etc. caused by cystine stones. Sometimes pyelonephritis or cystitis is caused by a secondary infection.

Therapeutic methods can be classified into two surgical methods, namely an operative removal of cystine stones and a destruction of cystine stones by a shock wave, and a dissolution of cystine stones. For dissolution, a fluid intake method, an alkalization method and a medicinal method with D-penicillamine or tiopronin are known (Urol. Clin. North. Am., 14, 339 (1987)).

If a cystine stone is removed by the surgical operation, the cystinuria patients can be released from the direct complaints. However the latter methods, namely the dissolution, still contain a problem of recurrence of cystine stone formation. Furthermore, there exist problems in the surgical methods. For example, the stone sometimes exists at a difficult place to be removed by an operation, and the cystine stone can be hardly destructed by the shock wave because the stone is harder than other kinds of stones. Therefore, the latter method, which can dissolve the cystine stone and prevent a recurrence of the stone formation, is very important for treatment of cystinuria.

However, the fluid intake method and alkalization method have some disadvantages. For example, in the fluid intake method, it is necessary for an adult patient to drink 4-6 liters of water a day and such large water intake is very hard to a patient. In the alkalization method, pH of the urine is raised to dissolve the cystine stones by administration of alkali such as sodium hydrogen carbonate, while it gives good conditions to form phosphate stones.

Therefore, it was devised to convert cystine into a water soluble mixed disulfide by administration of a medical substance having a sulfhydryl group to dissolve the cystine stone and further to prevent a recurrence of the stone formation. D-penicillamine, a medical substance applied first, was effective, but had a disadvantage of serious side effects. It was reported that the use of tiopronin, α-mercaptopropionylglycine, instead of D-penicillamine can reduce the side effects (Proc. Soc. Exptl. Biol. & Med., 129, 927 (1968), Urol. Clin. North. Am., 14, 339 (1987)). However, more effective and safer medical substances are desired for treatment of cystinuria.

Bucillamine, a main ingredient of this invention, has been known as a safe medical substance and to be useful as an anti-rheumatic, a liquefactant of sputum, a suppressant of liver disorders or an anti-cataract agent (Japanese Patent Publications 11888/1985, 5388/1981, 13922/1987 and 13964/1988). It is known that bucillamine is useful in various therapeutic fields, but an application to cystinuria has never been studied.

DETAILED DESCRIPTION OF THE INVENTION

This invention relates to a method for treatment of cystinuria by administration of bucillamine of the formula [I] or pharmaceutically acceptable salts thereof.

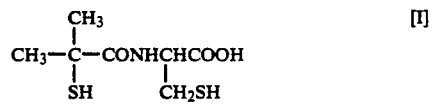

Examples of pharmaceutically acceptable salts are sodium salt and potassium salt.

Cystinuria is a hereditary disorder characterized by an excessive urinary excretion of cystine etc. and causes a cystine stone formation in urinary tract. Medicinal methods are applied most effectively for treatment of cystinuria. It is known that tiopronin, showing little side effects, can dissolve the cystine stone and prevent a recurrence of cystine stone formation and is useful for treatment of cystinuria. We studied to find more effective medical substances than tiopronin.

As the result of our precise study, we found that bucillamine showed a superior effect on cystinuria. We examined the utility of bucillamine for cystinuria by in vitro test, in which bucillamine was added to buffer solution of cystine and decrease of the concentration of cystine was measured. Tiopronin, a reference compound, was also tested in the same conditions. As shown in the article of pharmacological test in detail, bucillamine clearly decreased the concentration of cystine in buffer solution more effectively than tiopronin. The result proved that bucillamine is useful for treatment of cystinuria.

Bucillamine or salts thereof can be administered orally or parenterally. As the dosage forms, tablets of bucillamine are marketed, and tablet, granule, powder and injections disclosed in Japanese Patent Publications 5388/1981 and 11888/1985, etc. can be used. Further, bucillamine or salts thereof can be formulated in an irrigating solution to dissolve cystine stones by a renal irrigation.

The dosage of bucillamine or salts thereof is adjusted depending on the symptom, dosage from, age, etc. In case of the oral dose, the usual daily dosage is 10-3000 mg, preferably 50-1500 mg or 100-1200 mg, which can be given in one or a few divided doses.

EXAMPLE

Examples of preparation of the irrigating solution are shown below.

| Formulation 1 | |
|---|---|
| bucillamine | 5 g |
| sodium hydroxide | q.s. |
| distilled water for injection | q.s. |
| total | 100 ml |

Preparation method:
Bucillamine is added to 80 ml of distilled water for injection and pH of the solution is adjusted to 7 with sodium hydroxide. Distilled water for injection is added to the solution to make the total volume 100 ml.

The following irrigating solution of formulation 2 can be prepared by the similar method.

| Formulation 2 | |
|---|---|
| bucillamine | 1 g |
| sodium hydroxide | q.s. |
| distilled water for injection | q.s. |
| total | 100 ml |

Pharmacological Test

We examined the utility of bucillamine on cystinuria by an in vitro test, in which bucillamine was added to the buffer solution of cystine and a decrease of the concentration of cystine was measured. Tiopronin, a reference compound, was also tested in the same conditions.

Experimental Method

Cystine was dissolved in phosphate buffer solution (0.067M, pH 6.5) in a concentration of 500 μg/ml. Bucillamine was added to the solution in a concentration of 250 or 500 μg/ml. The mixture was incubated at 37° C. After 4 hours, the concentration of cystine was measured by a high performance liquid chromatography. As a reference, tiopronin was tested in the same conditions.

Result

The result is shown in Table 1 by decrement (%) of the concentration of cystine.

TABLE 1

| medical substance | amount of medical substance (μg/ml) | decrement of the concentration of cystine (%) |
|---|---|---|
| bucillamine | 250 | 60.6 |
|  | 500 | 87.8 |
| tiopronin | 250 | 48.5 |
|  | 500 | 75.3 |

As shown in Table 1, bucillamine clearly decreases the concentration of cystine in buffer solution more effectively than tiopronin.

What we claim is:

1. A method for treatment of cystinuria which comprises administering to a patient in need for said treatment bucillamine or a pharmaceutically acceptable salt thereof in an effective amount.

2. The method of claim 1, wherein the pharmaceutically acceptable salt is selected from the group consisting of a sodium salt and a potassium salt.

3. The method of claim 1, wherein the bucillamine is administered orally.

4. The method of claim 1, wherein the bucillamine is administered parenterally.

5. The method of claim 1, wherein the bucillamine is administered in the form of a tablet, granule, powder or injection.

6. The method of claim 1, wherein the bucillamine is administered by a renal irrigation.

7. The method of claim 1, wherein the bucillamine is administered orally at a dose of 10 to 3000 mg per day.

8. The method of claim 7, wherein the dose is 50 to 1500 mg per day.

9. The method of claim 7, wherein the dose is 100 to 1200 mg per day.

10. The method of claim 1, wherein the bucillamine is administered as an irrigation solution in combination with sodium hydroxide and distilled water.

* * * * *